United States Patent
Akerstrom et al.

(10) Patent No.: US 10,857,510 B2
(45) Date of Patent: Dec. 8, 2020

(54) BIOPROCESS MIXER

(71) Applicant: Global Life Sciences Solutions USA LLC, Marlborough, MA (US)

(72) Inventors: Patrik Berndt Akerstrom, Uppsala (SE); Richard Lee Damren, Marlborough, MA (US); Colin R. Tuohey, Marlborough, MA (US); Thomas Erdenberger, Marlborough, MA (US); Jonathan Kenney, Marlborough, MA (US); David Lawrence Brazell, Westborough, MA (US); Wei Jin, Westborough, MA (US); Roberto Miguel Cabral, Marlborough, MA (US); Sampath Telikcherla Kandala, Marlborough, MA (US)

(73) Assignee: Global Life Sciences Solutions USA LLC, Marlborough, MA (US)

( * ) Notice: Subject to any disclaimer, the term of this patent is extended or adjusted under 35 U.S.C. 154(b) by 97 days.

(21) Appl. No.: 15/565,438

(22) PCT Filed: Apr. 11, 2016

(86) PCT No.: PCT/EP2016/057884
§ 371 (c)(1),
(2) Date: Oct. 10, 2017

(87) PCT Pub. No.: WO2016/166046
PCT Pub. Date: Oct. 20, 2016

(65) Prior Publication Data
US 2018/0126344 A1    May 10, 2018

Related U.S. Application Data

(60) Provisional application No. 62/148,371, filed on Apr. 16, 2015.

(51) Int. Cl.
| | | |
|---|---|---|
| *B01F 13/08* | (2006.01) | |
| *C12M 1/06* | (2006.01) | |
| *B01F 15/00* | (2006.01) | |

(52) U.S. Cl.
CPC ...... *B01F 13/0827* (2013.01); *B01F 15/0085* (2013.01); *B01F 15/00863* (2013.01); *C12M 27/02* (2013.01); *B01F 2215/0073* (2013.01)

(58) Field of Classification Search
CPC .... C12M 27/02; C12M 23/14; B01F 13/0827; B01F 15/00863; B01F 15/0085; B01F 2215/0073
See application file for complete search history.

(56) References Cited

U.S. PATENT DOCUMENTS

| | | |
|---|---|---|
| 3,919,053 A | 11/1975 | Nazemi |
| 7,153,021 B2 | 12/2006 | Goodwin et al. |

(Continued)

FOREIGN PATENT DOCUMENTS

| | | |
|---|---|---|
| CA | 2264205 | 2/1998 |
| JP | S61-212278 A | 9/1986 |
| WO | 2005/068059 A1 | 7/2005 |

OTHER PUBLICATIONS

PCT International Search Report and Written Opinion for PCT Application No. PCT/EP2016/057884 dated Jul. 14, 2016 (13 pages).

(Continued)

*Primary Examiner* — Michael L Hobbs
(74) *Attorney, Agent, or Firm* — Eversheds Sutherland (US) LLP (57) ABSTRACT

A bioprocess mixer (1), which comprises: —a support vessel (2) with at least one side wall (3, 4, 5, 6) and a bottom wall (7), where the walls define a support vessel inner volume (8), and at least a first (9) and a second (10) magnetic impeller drive unit; and —a flexible bag (11, 111) adapted to fit inside (Continued)

the support vessel inner volume, where the bag has at least one bag side wall (12, 112, 13, 113, 14, 15), a bag bottom wall (16, 116) and a bag top wall (17, 117) defining a bag inner volume (18), and at least a first (19) and a second (20) magnetic impeller rotatably attached to a bag wall in the bag inner volume.

37 Claims, 6 Drawing Sheets

(56) References Cited

U.S. PATENT DOCUMENTS

| | | | |
|---|---|---|---|
| 8,690,129 B2 | 4/2014 | Ludwig et al. | |
| 9,550,157 B2 | 1/2017 | Erdenberger et al. | |
| 9,675,947 B2 | 6/2017 | Gebauer et al. | |
| 2006/0092761 A1 | 5/2006 | Terentiev | |
| 2007/0165485 A1 | 7/2007 | Cai | |
| 2007/0253288 A1* | 11/2007 | Mennenga | B01F 11/0082 366/274 |
| 2007/0263484 A1 | 11/2007 | Terentiev | |
| 2008/0131957 A1* | 6/2008 | Ryan | C12M 23/28 435/289.1 |
| 2008/0139865 A1* | 6/2008 | Galliher | B08B 15/02 588/249 |
| 2009/0035856 A1* | 2/2009 | Galliher | C12M 29/10 435/383 |
| 2009/0130757 A1 | 5/2009 | Terentiev | |
| 2010/0129899 A1 | 5/2010 | Oosterhuis et al. | |
| 2010/0149908 A1* | 6/2010 | Singh | B01F 15/065 366/276 |
| 2011/0038222 A1* | 2/2011 | Ludwig et al. | B01F 3/04269 366/102 |
| 2013/0011896 A1* | 1/2013 | Strehler | C05F 17/0027 435/167 |
| 2013/0101982 A1* | 4/2013 | Goodwin | B01F 7/0095 435/3 |
| 2013/0186834 A1 | 7/2013 | Vicalvi et al. | |
| 2017/0073624 A1* | 3/2017 | Stankowski | C12M 23/14 |

OTHER PUBLICATIONS

Japanese Office Action for JP Application No. 2017-552083 dated Jan. 6, 2020 (9 pages with English translation).
Chinese Office Action for CN Application No. 201680021814.0 dated Apr. 25, 2020 (48 pages with English translation).

* cited by examiner

BIOPROCESS MIXER

CROSS REFERENCE TO RELATED APPLICATIONS

This application claims the priority benefit of PCT/EP2016/057884 filed on Apr. 11, 2016 which claims priority benefit of U.S. Provisional Application No. 62/148,371 filed Apr. 16, 2015. The entire contents of which are hereby incorporated by reference herein.

TECHNICAL FIELD OF THE INVENTION

The present invention relates to mixers for bioprocess use, and more particularly to a mixer with a single-use bag. The invention also relates to a bioreactor, to a support vessel and to methods for mixing and for cultivation of cells.

BACKGROUND OF THE INVENTION

The bioprocessing industry has traditionally used stainless steel systems and piping in manufacturing processes for expression and purification of therapeutic proteins etc. These devices are designed to be reused after cleaning and/or sterilization. Cleaning and sterilization are however costly labor-intensive operations. Moreover, the installed cost of these traditional systems with the requisite piping and utilities is often prohibitive. Furthermore, these systems are typically designed for a specific process, and cannot be easily reconfigured for new applications. These limitations have led to adoption of a new approach over the last fifteen years—that of using plastic, single-use disposable bags and tubing, to replace the usual stainless steel tanks.

In large-scale operations, the preferred solution is to use flexible bags supported by an outer stainless steel support vessel. This allows single-use operation in scales up to several cubic meters. However, at such large scales, mixing efficiency becomes an issue and accordingly there is a need for large scale single-use systems with improved mixing.

SUMMARY OF THE INVENTION

One aspect of the invention is to provide an efficient bioprocess mixer with a single-use bag in a support vessel. This is achieved with a mixer as defined in claim 1.

One advantage is that a rapid mixing of large volumes can be achieved. Further advantages are that the mixer can easily be moved between different locations, that the mixer can have a low center of gravity and that an efficient heat transfer can be achieved.

A second aspect of the invention is to provide a bioreactor with efficient agitation. This is achieved with a bioreactor as defined in the claims.

A third aspect is to provide a support vessel for a bioprocess mixer or a bioreactor. This is achieved with a support vessel as defined in the claims.

A fourth aspect is to provide an efficient method of preparing a liquid mixture. This is achieved with a method as defined in the claims.

A fifth aspect is to provide an efficient method of cultivating cells. This is achieved with a method as defined in the claims.

Further suitable embodiments of the invention are described in the dependent claims.

DEFINITIONS

To more clearly and concisely describe and point out the subject matter of the claimed invention, the following definitions are provided for specific terms that are used in the following description and the claims appended hereto.

The singular forms "a" "an" and "the" include plural referents unless the context clearly dictates otherwise. Approximating language, as used herein throughout the specification and claims, may be applied to modify any quantitative representation that could permissibly vary without resulting in a change in the basic function to which it is related. Accordingly, a value modified by a term such as "about" is not to be limited to the precise value specified. Unless otherwise indicated, all numbers expressing quantities of ingredients, properties such as molecular weight, reaction conditions, so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the embodiments of the present invention. At the very least each numerical parameter should at least be construed in light of the number of reported significant digits and by applying ordinary rounding techniques.

Any directional terms such as "top", "bottom", "above", "below" "up", "down" and "height" herein refer to the devices as they appear in the drawings. Joinder references (e.g., joined, attached, coupled, connected, and the like) are to be construed broadly and may include intermediate members between a connection of elements and relative movement between elements. As such, joinder references do not necessarily imply that two elements are connected directly and in fixed relation to each other. Further, various elements discussed with reference to the various embodiments may be interchanged to create entirely new embodiments coming within the scope of the present invention.

DETAILED DESCRIPTION OF EMBODIMENTS

Figure 1:
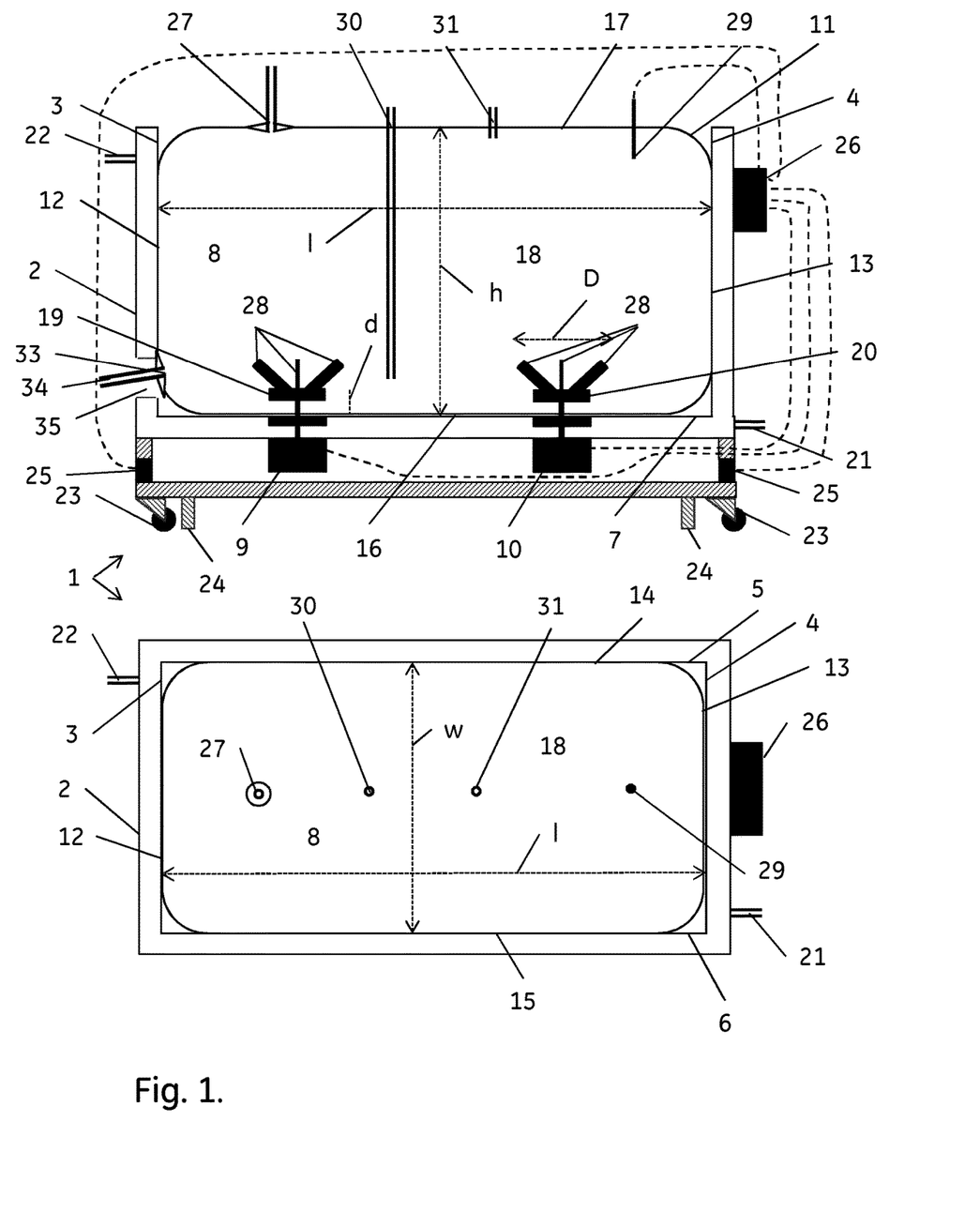
FIG. 1 shows a mixer according to the invention with a bag in a support vessel, side view and top view.
Figure 2:
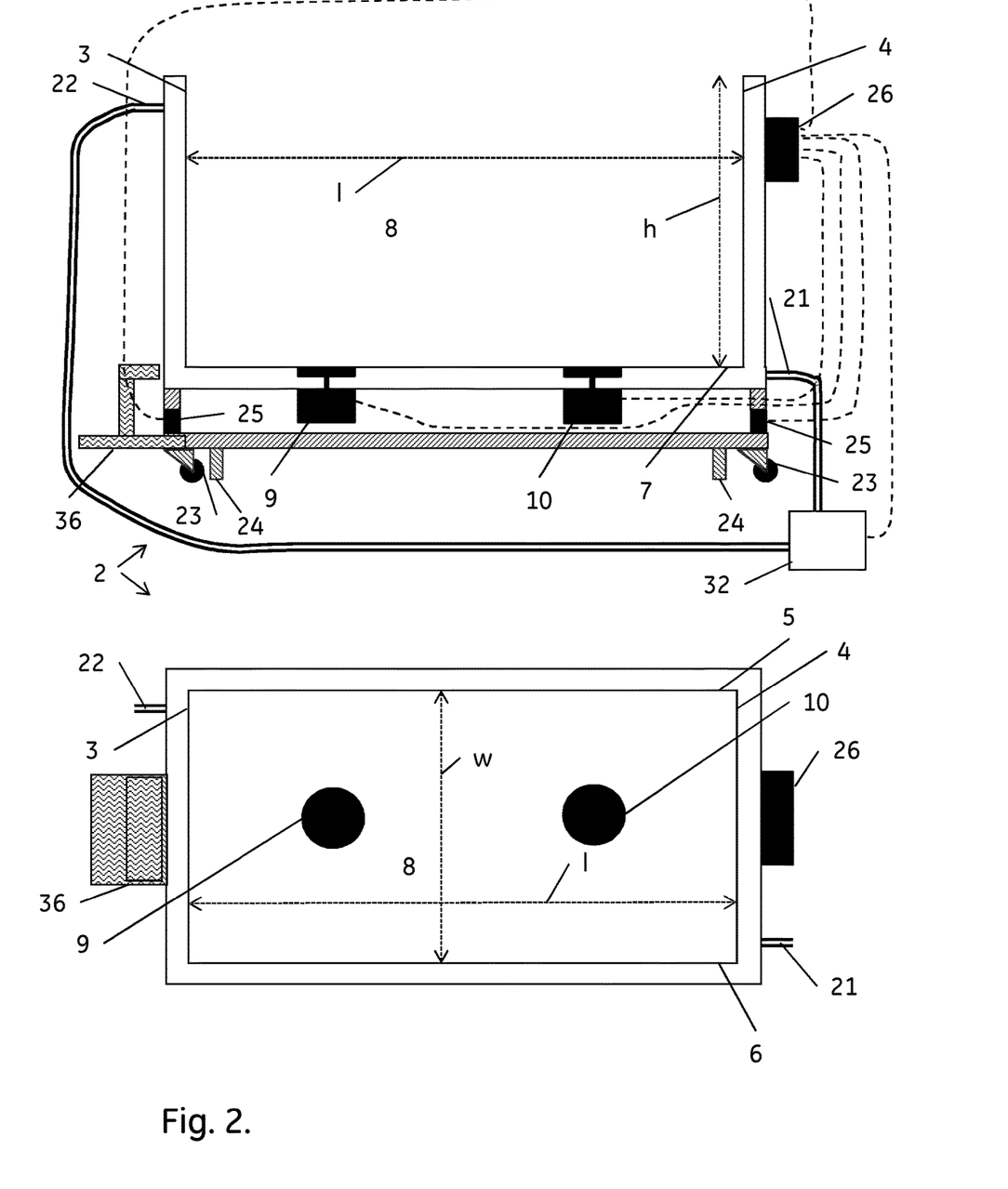
FIG. 2 shows a support vessel according to the invention, side view and top view.

In one aspect, illustrated by FIGS. 1-6, the present invention discloses a bioprocess mixer 1, which comprises:

a) A support vessel 2 comprising at least one side wall 3,4,5,6, such as at least one upstanding side wall 3,4,5,6, and a bottom wall 7, where the walls define a support vessel inner volume 8. The support vessel comprises at least a first 9 and a second 10 magnetic impeller drive unit and may optionally comprise further magnetic impeller drive units, such as e.g. one, two, three or four further units. The magnetic impeller drive units can e.g. be mounted in or behind/below one or more of the side walls and the bottom wall. They can all be mounted in, behind or below the same wall or they can be mounted in, behind or below different walls. A magnetic impeller drive unit may e.g. be a motor with a rotating shaft to which one or more magnets are fixed such that they rotate with the shaft and provide a rotating magnetic field capable of driving a magnetic impeller. The support vessel may further have a top cover (not shown), to protect the bag and to provide insulation.

b) A flexible bag 11;111 adapted to fit inside the support vessel inner volume, where the bag has at least one bag side wall 12;112,13;113,14,15, a bag bottom wall 16;116 and a bag top wall 17;117, which together define a bag inner volume 18. The bag has at least a first 19 and a second 20 magnetic impeller rotatably attached to one or more bag walls in the bag inner volume (i.e. on the inside of the bag wall) and may optionally comprise further magnetic impellers, such as one, two, three or four further impellers. The magnetic impellers are suitably located such that when the bag is fitted inside the support vessel, each impeller is adjacent to a magnetic impeller drive unit, allowing the drive unit to drive the impeller by action of the rotating magnetic field on one or more magnets in the impeller. Suitably, the magnetic impellers are capable of rotating independently of each other, e.g. by each being mounted to a separate axis. The rotatable attachment to the bag wall(s) can e.g. be constructed as described in U.S. Pat. No. 6,758,593, 7,481, 572 or WO2014116165, which are hereby incorporated by reference in their entireties. The bag may be manufactured from one or more sheets of flexible material, e.g. a plastic film or a multilayer flexible plastic laminate. Each bag wall may comprise either a homogeneous part of a single sheet or a plurality of sheet parts joined by welding. Suitably the bag is a three-dimensional bag as known in the art of single-use bags for bioprocess purposes (see e.g. US20020131654, US20040245144 or WO2013112963A1, which are hereby incorporated by reference in their entireties). The bag may conform to or essentially conform to the support vessel inner volume, such that it fits closely to the inside of the support vessel. The joints between the walls of the bag may be right angled or generally right angled with a radius of curvature.

Figure 3:
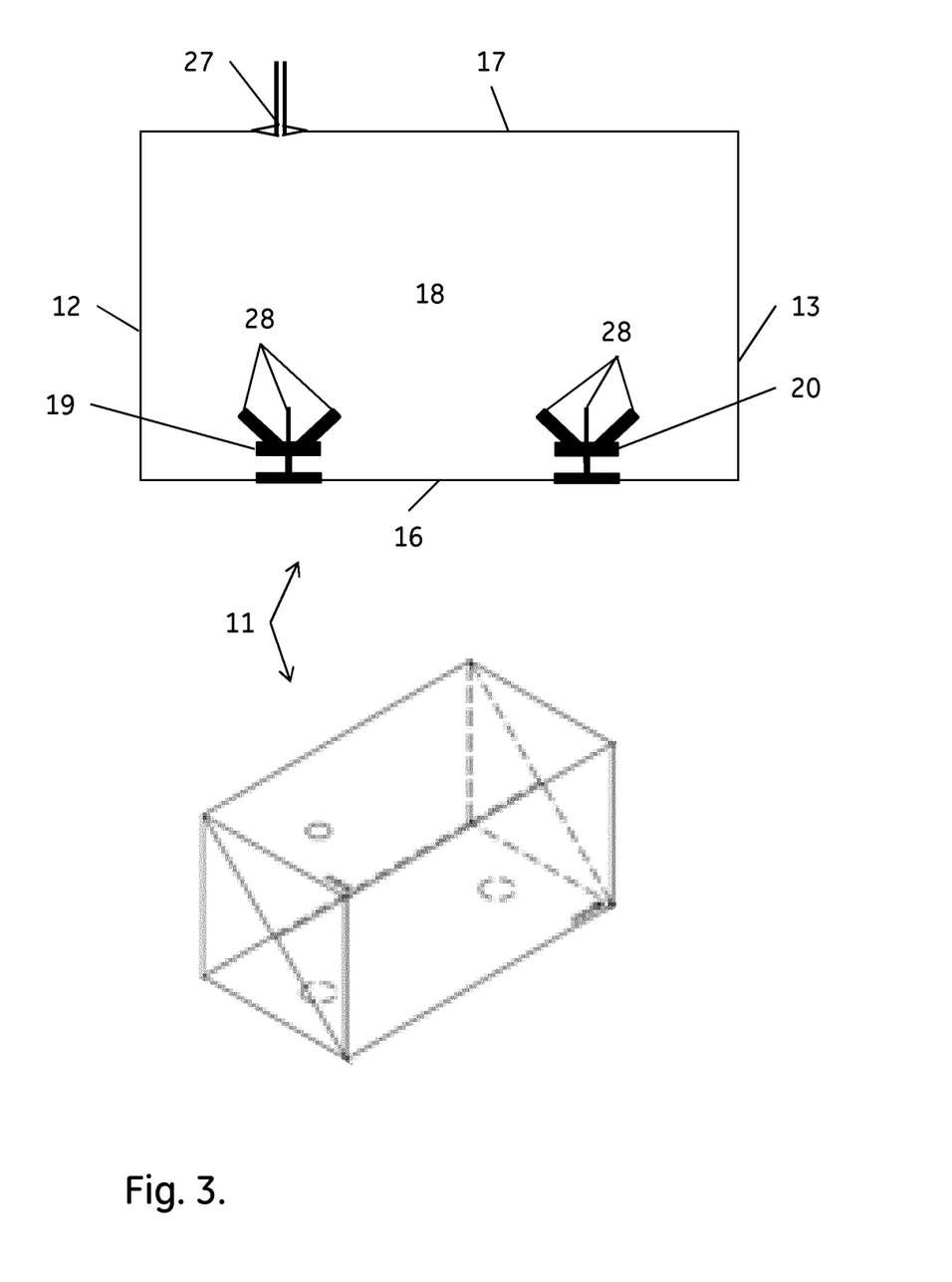
FIG. 3 shows a bag for use in the invention, side view and oblique view (impellers not shown in the oblique view).

In certain embodiments, at least the first and second magnetic impeller drive units 9,10 are mounted in or below the bottom wall 7 of the support vessel and at least the first and second magnetic impellers 19, 20 are rotatably attached to the bag bottom wall 16 in the bag inner volume, suitably adjacent to the drive units 9,10.

In some embodiments, the support vessel comprises four side walls 3,4,5,6 and a bottom wall 7 defining a generally cuboid support vessel inner volume 8 having a length l, a width w and a height h. The four side walls and the bottom wall may each have a rectangular shape and they may meet at right angles or approximately right angles to each other, forming a shape with generally rectangular top and side projections. Correspondingly, the flexible bag has in these embodiments a generally cuboid shape with generally rectangular top and side projections, with a bag inner volume 18 defined by four bag side walls 12;112,13;113,14,15, a bag bottom wall 16;116 and a bag top wall 17;117. The four bag side walls, the bottom wall and the top wall may each have an approximately rectangular shape and adjacent walls may be at right angles or approximately right angles to each other.

In certain embodiments, the support vessel inner volume has a length-to-width ratio (l/w) of at least 1.5, such as 1.5-3 or 1.5-2. A high length-to-width ratio enables movement of mixers with high inner volumes between different locations, e.g. through door openings, and when the impeller arrangements described above are used, excellent agitation can be achieved also at high length-to-width ratios.

In some embodiments, the support vessel inner volume has a height-to-width ratio (h/w) of 0.7-2, such as 0.7-1.3. A low height-to-width ratio also facilitates movement of large mixers between different locations and allows for a low center of gravity. A low center of gravity is important for stability and prevents the risk of the mixer tipping over. It is e.g. possible to mount external suspended steps 36 on the support vessel to allow easy access to the support vessel inner volume and the bag without risk of the mixer or support vessel tipping over when a person climbs the steps.

In certain embodiments, the support vessel inner volume and/or bag inner volume is at least 1.5 m$^3$, such as at least 2 m$^3$ or 2-5 m$^3$ or 2-3 m$^3$. The demands on good agitation are particularly high in larger scales but can be fulfilled with the impeller arrangements described above.

In some embodiments, the support vessel is double-mantled and comprises inlet 21 and outlet 22 ports for a temperature-control fluid. The temperature-control fluid can be conveyed, e.g. by pumping, from a supply 32 of temperature-control fluid, which can be e.g. a thermostated water or oil bath, a steam supply etc. In most bioprocess applications, the desired temperature is within the 4-40° C. interval and thermostated water is commonly used.

In certain embodiments, the mixer is mounted on casters 23 with floor locks 24. The mixer can be moved on the casters and the floor locks can suitably be applied before filling the bag with liquid. Casters and floor locks can be integrated or they can be mounted separately.

In some embodiments, the mixer is supported by load cells 25. The load cells, which can be electrically or electromagnetically connected to a control unit, allow continuous monitoring of the degree of filling of the bag.

In certain embodiments, the mixer further comprises a control unit 26, electrically or electromagnetically connected to said at least first and second magnetic impeller drive units and optionally to the load cells and/or to a supply 32 of heat-control fluid. The control unit may e.g. be capable of individually controlling the rotation directions and rotation speeds of the at least first and second magnetic impeller drive units. This allows for full flexibility in the agitation profile, e.g. by selecting co-rotating or oppositely rotating impellers. When impellers with angled blades are used, the pumping direction of the impeller (up or down) will depend on the rotation direction. In some applications it can be advantageous to one impeller with a downwards pumping direction and one with an upwards pumping direction, while in other applications running all impellers with the same pumping direction may be preferred.

In certain embodiments, the flexible bag has at least one port 27,30,31;126,127;227,230,231 in said bag top wall. Through this port, liquid and solid components can be added to the inner volume of the bag and it is also possible to withdraw liquid from the bag via a dip-tube attached to the port. For withdrawal of liquid, it is however also possible to use a drain port 33 in the lower part of the bag, which port may be fluidically connected to tubing 34 passing through a hole 35 in a side wall or bottom wall of the support vessel. The bag may also comprise further ports, e.g. for addition of different components, for removal of samples and/or for adding or withdrawing gases.

Figure 6:
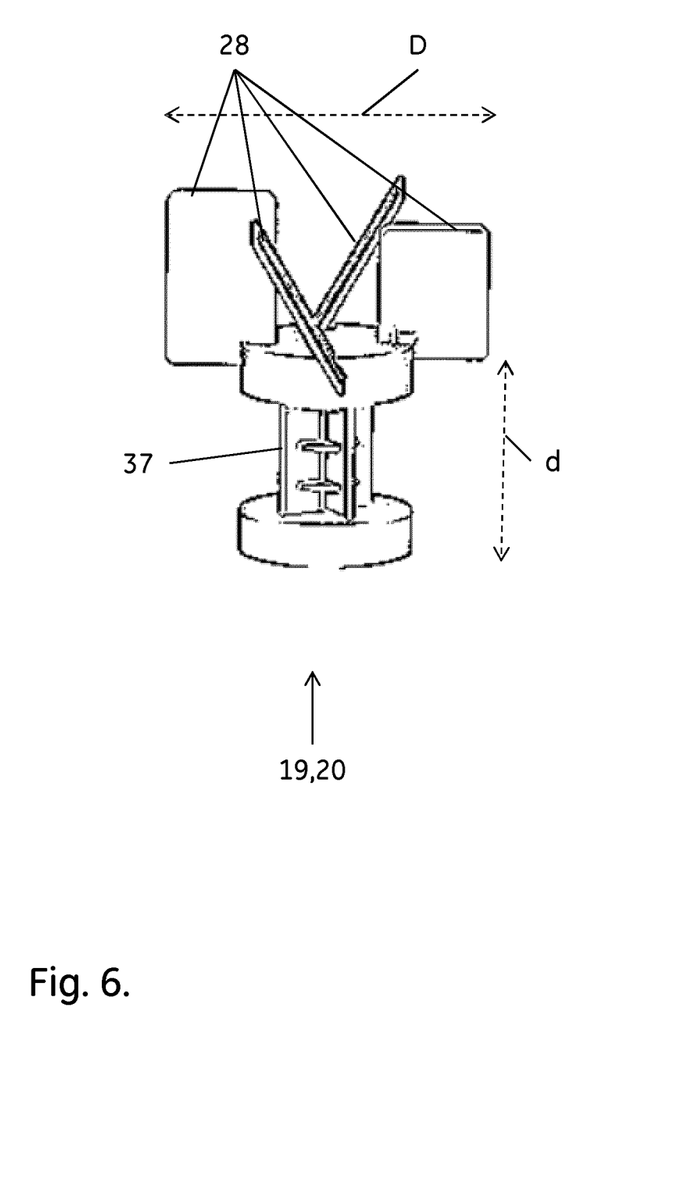
FIG. 6 shows an impeller for use with the invention, oblique view.

In some embodiments, said at least first and second magnetic impellers each have at least three, such as four, impeller blades 28. Two-blade impellers can also be used, as well as impellers with more than four blades, e.g. five or six blades. The impellers may e.g. have angled or vertically mounted impeller blades, which can be flat or curved depending on the application needs. The impellers may each be rotatably attached to a bag wall, e.g. the bag bottom wall, such that the shortest distance d from the impeller blades to any bag wall, e.g. the bag bottom wall, is at least 7 cm, such as at least 10 cm, such as 10-30 cm or 10-20 cm. The diameters D of the impellers can e.g. be at least 10 cm, such as at least 15 cm, or 10-40 cm, such as 15-25 cm.

In certain embodiments, the mixer further comprises one or more sensors 29 adapted to measure one or more properties in a liquid confined in the bag inner volume, such as conductivity, pH and/or temperature. The sensors can be used to verify that a sufficient homogeneity has been achieved in a mixing operation, typically by monitoring when a steady state has been reached. Alternatively, the sensor(s) can be used to monitor deliberate changes in a property and e.g. to stop the addition of a component when a particular value has been reached. An example is the titration of a buffer to a predetermined pH by addition of acid or base.

Figure 4:
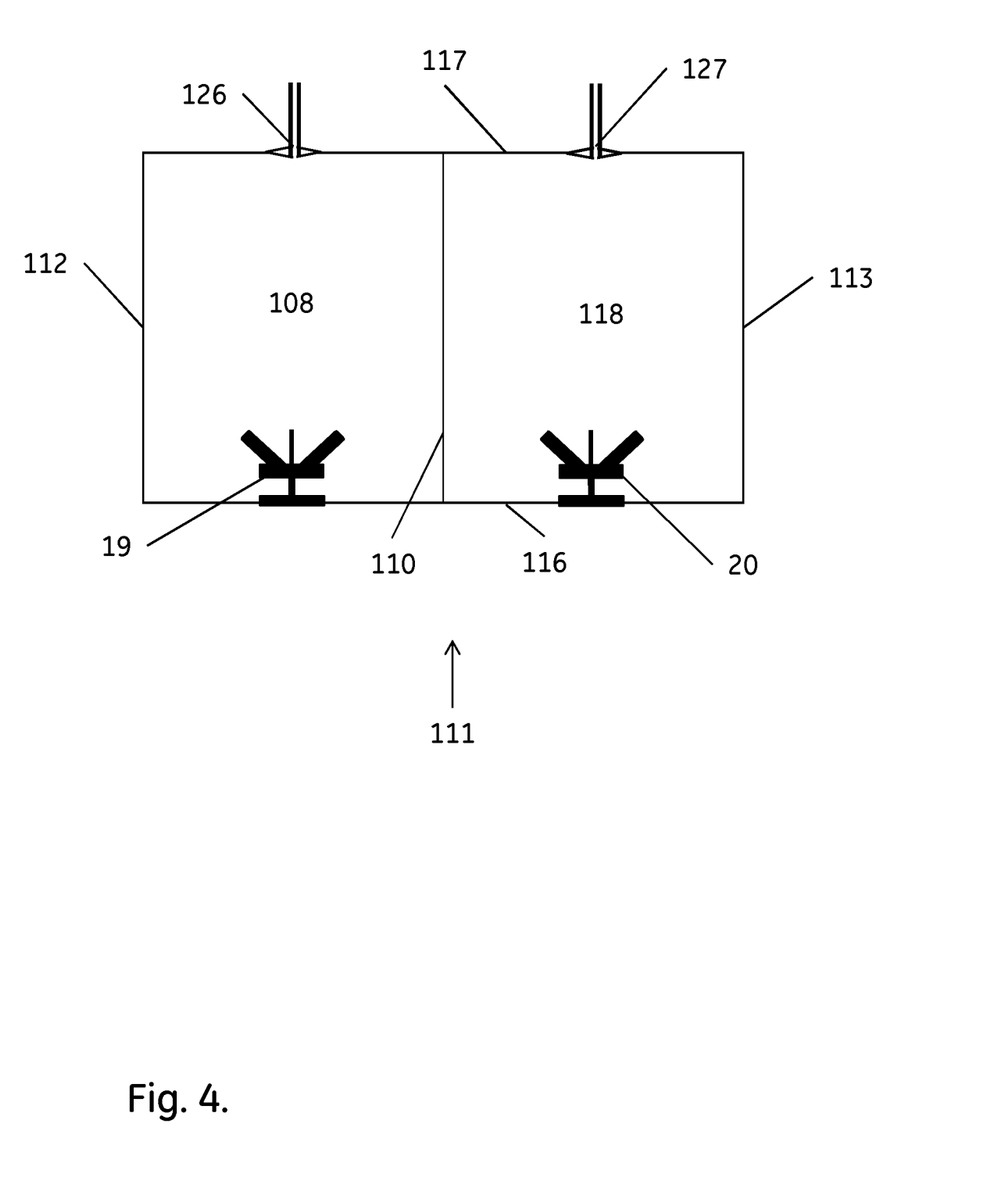
FIG. 4 shows an alternative bag for use with the invention, side view.

In some embodiments, illustrated by FIG. 4, the bag 111 comprises an interior wall 110, dividing the bag inner volume into at least two separate mixer compartments 108, 118, suitably with at least one port 126, 127 in each compartment. Suitably, one of said at least first and second magnetic impellers can be located in each compartment. This allows the preparation of more than liquid mixture, which can be needed in many situations. The possibility to use the same support vessel both as a large single-compartment mixer and with several independent mixer compartments adds flexibility to a bioprocess setup and reduces capital cost. The interior wall 110 may be a sheet of flexible plastic material, but it can also be a rigid wall, e.g. of a plastic or metallic material. Alternatively, the mixer may comprise two separate bags, with one of said at least first and second magnetic impellers located in each bag.

Figure 5:
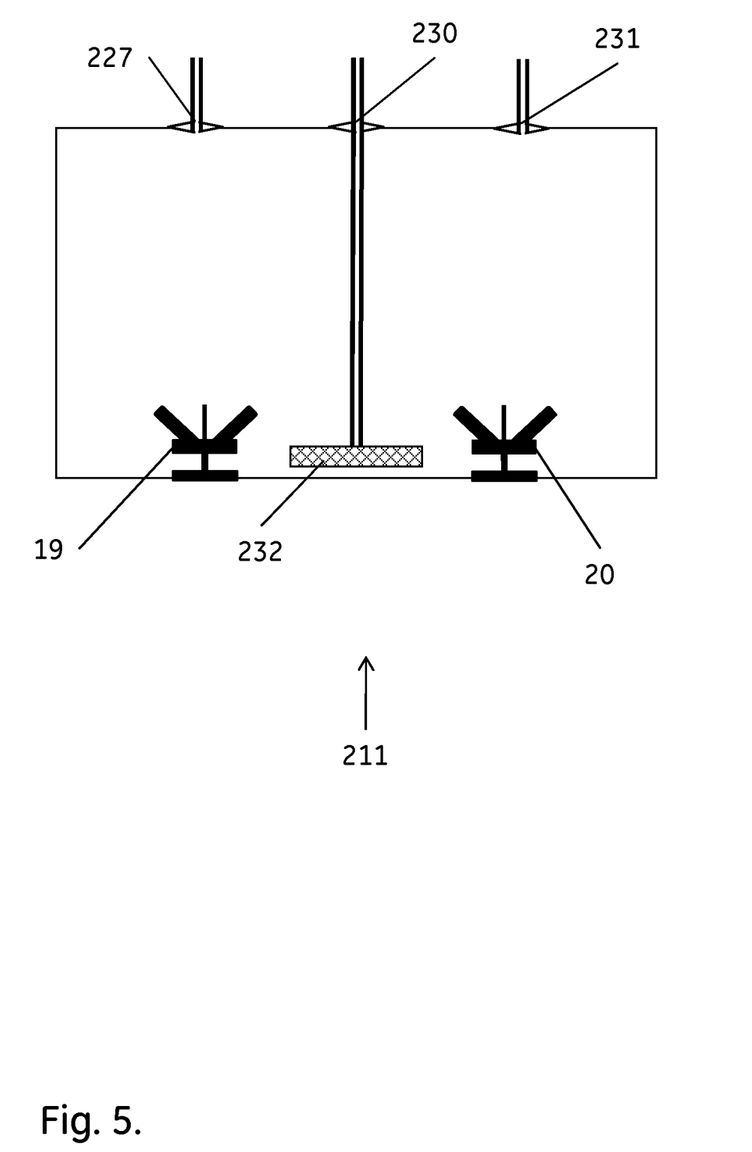
FIG. 5 shows an alternative bag for use with the invention, side view.

In a second aspect, the invention discloses a bioreactor, which comprises a mixer as disclosed in any of the above embodiments. The bag 11;211 of the mixer may further comprise at least one gas inlet port 30;230 and at least one gas outlet port 31;231. One or more gas inlet ports 230 may e.g. be fluidically connected to one or more spargers 232 in the bag inner volume to provide aeration of a cell culture in the bag. One or more magnetically driven impeller may also be arranged to disperse gas from a sparger into the inner volume of the bag. The bioreactor may further comprise additional sensors, e.g. for monitoring oxygen concentration, carbon dioxide concentration and/or concentrations of other nutrients or metabolites. To minimize foaming, the bioreactor may comprise an antifoam addition port and/or it may comprise a magnetically driven impeller in a top region of the bag, adapted to act as a foam breaker. A foam breaker impeller may e.g. be a turbine rotating in the foam above the liquid level of the bioreactor, causing the acceleration of the foam liquid towards the side wall(s) of the bag where it can return to the culture by action of gravity. The foam breaker impeller may be one of the first and second magnetic impellers, but it may also be an additional magnetic impeller. It is further contemplated that the bioreactor may comprise a plurality of magnetically driven foam breaker impellers.

In a third aspect, illustrated by FIG. 2, the invention discloses a support vessel 2 for a bioprocess mixer or a bioreactor, comprising at least one side wall 3,4,5,6 and a bottom wall 7, said walls defining a support vessel inner volume 8, and in or below said bottom wall comprising at least a first 9 and a second 10 magnetic impeller drive unit.

In some embodiments, the support vessel comprises four side walls 3,4,5,6 and a bottom wall 7 defining a generally cuboid support vessel inner volume 8 having a length 1, a width w and a height h. The support vessel inner volume can e.g. have a length-to-width ratio (l/w) of at least 1.5, such as 1.5-3 or 1.5-2 and/or it can e.g. have a height-to-width ratio (h/w) of 0.7-1.3. The support vessel inner volume can e.g be at least 1.5 $m^3$, such as at least 2 $m^3$ or 2-5 $m^3$ or 2-3 $m^3$.

In certain embodiments, the support vessel is double-mantled and comprises inlet 21 and outlet 22 ports for a temperature-control fluid, which can e.g. originate from supply 32 of temperature-control fluid.

In some embodiments, the support vessel is mounted on casters 23 with floor locks 24. It can also be supported by load cells 25 and it can comprise external suspended steps 36.

In certain embodiments, the support vessel further comprises a control unit 26, which is electrically or electromagnetically connected to said at least first and second magnetic impeller drive units and optionally to said load cells and/or to a supply 32 of heat-control fluid. The control unit may be capable of individually controlling the rotation directions and rotation speeds of the at least first and second magnetic impeller drive units.

In a fourth aspect, the invention discloses a method of preparing a liquid mixture, comprising the steps of:

a) Providing the mixer 1 as disclosed above. This may include the provision of the support vessel 2 as disclosed above and a corresponding bag 11;111. The bag is mounted in the support vessel and all applicable ports and sensors are connected as appropriate.

b) Adding at least one liquid and at least one further component to the bag inner volume 18. The liquid can e.g. be water, a buffer, a salt solution, a cell culture broth or an eluate from a chromatography column, while further components may include buffer components, salts, acids, bases etc.

c) Mixing the at least one liquid and the at least one further component under agitation provided by at least the first 19 and second 20 magnetic impellers.

In some embodiments, at least one further component comprises a solid substance, which can e.g. be a powder or a granulate, e.g. a powdered or granulated salt or buffer species. The liquid mixture may then be a solution, or optionally a suspension, of at least this solid substance which dissolves or suspends in the liquid phase of the mixture.

In certain embodiments, the liquid mixture comprises an aqueous buffer. The liquid mixture may be a ready-to-use buffer, but it may also be e.g. a buffer concentrate intended to be diluted and/or adjusted (e.g. by pH or salt adjustment) before use.

In some embodiments, during step c) at least one property of the liquid mixture, such as conductivity and/or pH, is monitored to determine if the mixture is homogeneous. This can suitably be done by using sensor(s) 29 and control unit 26 to determine when a steady state in the relevant signal(s) has been reached.

In a fifth aspect, the invention discloses a method of cultivating cells, comprising the steps of:

a) providing the bioreactor as disclosed above;

b) adding a culture medium and cells to said bag inner volume; and c) cultivating cells in said bioreactor under agitation provided by said at least first and second magnetic impellers.

In some embodiments, in step c) a gas, e.g. air, is conveyed into the bag inner volume via one or more gas inlet ports and exhaust gas is conveyed out of the bag inner volume via one or more gas outlet ports. As discussed above, the gas may be provided to the culture via one or more spargers and it may be dispersed with one or more magnetic impellers. Foaming may be reduced by one or more magnetic foam breaker impellers.

Example 1—Liquid-Liquid Mixing

The experiment was carried out in a 2500 L plastic bag with two magnetic impellers in the bottom, confined in an elongated right-angled cuboid support vessel with inner dimensions 208 cm (length)×112 cm (width)×114 cm (height) and with two magnetic impeller drive motors symmetrically arranged in the bottom wall. The support vessel was double-mantled and thermostated to 40° C. The bag was equipped with four conductivity sensors in different positions. The impellers had four angled blades each, designed as illustrated in FIG. 6, with a 10 cm extension piece 37, where the distance d from the bag bottom wall to the impeller blades was 11.5 cm and the impeller diameter D was 18.7 cm.

The bag was filled with 2300 L filtered tap water, the agitation was set to 200 rpm with opposite rotation directions of the impellers (one pumping upwards and one downwards) and the water temperature was allowed to reach 40° C. The conductivity was monitored with the four sensors, which all gave constant signals. 10 L of 2.5 M NaCl solution was then added to the bag in one shot and the time until the conductivity sensors gave constant signals was measured. This process was repeated twice with two more shots of 10 L 2.5 M NaCl. The times until constant signals in the three 200 rpm experiments were: 34 s, 52 s and 35 s.

The agitation was then set to 350 rpm (still with opposite rotation directions) and three more shots of 10 L 2.5 M NaCl solution were added. The times until constant signals in the three 350 rpm experiments were: 20 s, 22 s and 21 s.

Example 2—Solid-Liquid Mixing

The same setup as in Example 1 was used, with 2300 L filtered tap water at 40° C. With the agitation set to 200 rpm (again opposite rotation directions), 8 kg of NaCl powder was added in one shot and the time to constant conductivity signals was measured. This was repeated with two more shots of 8 kg NaCl. The times until constant signals in the three 200 rpm powder experiments were: 121 s, 125 s and 129 s.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims. Any patents or patent applications mentioned in the text are hereby incorporated by reference in their entireties, as if they were individually incorporated.

The invention claimed is:

1. A bioprocess mixer, comprising:
    a support vessel comprising at least one side wall and a bottom wall, said walls defining a support vessel inner volume, and at least a first and a second magnetic impeller drive unit; and
    a flexible bag adapted to fit inside said support vessel inner volume, said bag having at least one bag side wall, a bag bottom wall and a bag top wall defining a bag inner volume, with at least a first and a second magnetic impeller rotatably attached to one or more bag wall in said bag inner volume,
    wherein said support vessel inner volume has a length-to-width ratio of at least 1.5 for facilitating movement of the bioprocess mixer,
    wherein said support vessel inner volume has a height-to-width ratio of 0.7-2 for facilitating movement of the bioprocess mixer and stability,
    wherein said at least first and second magnetic impellers each have a base from which at least four impeller blades extend,
    wherein said at least first and second magnetic impellers each comprise a ribbed extension piece extending from the base away from the at least four impeller blades,
    wherein the at least four impeller blades includes diametrically opposed blade pairs, and
    wherein each of the at least four impeller blades is angled.

2. The bioprocess mixer of claim 1, wherein said at least first and second magnetic impeller drive units are mounted in or below said bottom wall and said at least first and second magnetic impellers are rotatably attached to said bag bottom wall in said bag inner volume.

3. The bioprocess mixer of claim 1, wherein:
    the support vessel comprises four side walls and a bottom wall defining a generally cuboid support vessel inner volume having a length, a width (w) and a height (h); and
    the flexible bag has a generally cuboid shape, with a bag inner volume defined by four bag side walls, a bag bottom wall and a bag top wall.

4. The mixer of claim 1, wherein said support vessel inner volume has a length-to-width ratio of 1.5-3.

5. The mixer of claim 1, wherein said support vessel inner volume has a height-to-width ratio of 0.7-1.3.

6. The mixer of claim 1, wherein said support vessel inner volume and/or bag inner volume is at least 1.5 m$^3$.

7. The mixer of claim 1, wherein said support vessel is double-mantled and comprises inlet and outlet ports for a temperature-control fluid.

8. The mixer of claim 1, which is mounted on casters with floor locks.

9. The mixer of claim 1, which is supported by load cells.

10. The mixer of claim 1 with external suspended steps mounted on the support vessel.

11. The mixer of claim 1, further comprising a control unit, electrically or electromagnetically connected to said at least first and second magnetic impeller drive units and optionally to said load cells and/or to a supply of heat-control fluid.

12. The mixer of claim 11, wherein rotation directions and rotation speeds of said at least first and second magnetic impeller drive units can be individually controlled by said control unit.

13. The mixer of claim 1, wherein said flexible bag has at least one port in said bag top wall.

14. The mixer of claim 1, wherein said at least first and second magnetic impellers each are rotatably attached to said bag bottom wall such that the distance from said impeller blades to said bag bottom wall is at least 7 cm.

15. The mixer of claim 1, wherein said at least first and second magnetic impellers each are rotatably attached to a bag wall such that the shortest distance from said impeller blades to a bag wall is at least 7 cm.

16. The mixer of claim 1, further comprising one or more sensors adapted to measure one or more properties in a liquid confined in the bag inner volume.

17. The mixer of claim 1, wherein said bag comprises an interior wall, dividing the bag inner volume into at least two separate mixer compartments.

18. A bioreactor, comprising the mixer of claim 1.

19. The bioreactor of claim 18, wherein said bag comprises at least one gas inlet port and at least one gas outlet port.

20. A support vessel for a bioprocess mixer or a bioreactor, comprising at least one side wall and a bottom wall, said walls defining a support vessel inner volume, and in or below said bottom wall comprising at least a first and a second magnetic impeller drive unit
wherein said support vessel inner volume has a length-to-width ratio of at least 1.5, and
wherein said support vessel inner volume has a height-to-width ratio of 0.7-2.

21. The support vessel of claim 20, comprising four side walls and a bottom wall defining a generally cuboid support vessel inner volume having a length, a width and a height.

22. The support vessel of claim 20, wherein said support vessel inner volume has a length-to-width ratio of 1.5-3.

23. The support vessel of claim 20, wherein said support vessel inner volume has a height-to-width ratio of 0.7-1.3.

24. The support vessel of claim 20, wherein said support vessel inner volume is at least 1.5 $m^3$.

25. The support vessel of claim 20, which is double-mantled and comprises inlet and outlet ports for a temperature-control fluid.

26. The support vessel of claim 20, which is mounted on casters with floor locks.

27. The support vessel of claim 20, which is supported by load cells.

28. The support vessel of claim 20, comprising external suspended steps.

29. The support vessel of claim 20, further comprising a control unit, electrically or electromagnetically connected to said at least first and second magnetic impeller drive units and optionally to said load cells and/or to a supply of heat-control fluid.

30. The support vessel of claim 29, wherein rotation directions and rotation speeds of said at least first and second magnetic impeller drive units can be individually controlled by said control unit.

31. A method of preparing a liquid mixture, comprising the steps of:
a) providing the mixer of claim 1;
b) adding at least one liquid and at least one further component to said bag inner volume; and
c) mixing the at least one liquid and the at least one further component under agitation provided by the first and second magnetic impellers.

32. The method of claim 31, wherein at least one further component comprises a solid substance, such as a powder or a granulate.

33. The method of claim 32, wherein said liquid mixture is a solution of at least said solid substance.

34. The method of claim 31, wherein said liquid mixture comprises an aqueous buffer.

35. The method of claim 31, wherein during step c) at least one property of the liquid mixture, such as conductivity and/or pH, is monitored to determine if the mixture is homogeneous.

36. A method of cultivating cells, comprising the steps of:
a) providing the bioreactor of claim 18;
b) adding a culture medium and cells to said bag inner volume; and
c) cultivating cells in said bioreactor under agitation provided by said at least first and second magnetic impellers.

37. The method of claim 36, wherein in step c) a gas is conveyed into said bag inner volume via one or more gas inlet ports and exhaust gas is conveyed out of said bag inner volume via one or more gas outlet ports.

* * * * *